United States Patent
Ahn et al.

(10) Patent No.: US 8,917,079 B2
(45) Date of Patent: Dec. 23, 2014

(54) REFERENCE POTENTIAL ADJUSTMENT DEVICE AND A MEASURING DEVICE EQUIPPED WITH THE SAME

(75) Inventors: Jin Hong Ahn, Yongin-si (KR); Young June Park, Seoul (KR)

(73) Assignee: SNU R&DB Foundation, Seoul (KR)

( * ) Notice: Subject to any disclaimer, the term of this patent is extended or adjusted under 35 U.S.C. 154(b) by 290 days.

(21) Appl. No.: 13/637,789

(22) PCT Filed: Feb. 16, 2011

(86) PCT No.: PCT/KR2011/001006
§ 371 (c)(1),
(2), (4) Date: Nov. 13, 2012

(87) PCT Pub. No.: WO2011/122765
PCT Pub. Date: Oct. 6, 2011

(65) Prior Publication Data
US 2013/0057251 A1 Mar. 7, 2013

(30) Foreign Application Priority Data

Mar. 31, 2010 (KR) .......... 10-2010-0028922
Jun. 1, 2010 (KR) .......... 10-2010-0051966

(51) Int. Cl.
*G01R 17/02* (2006.01)
*G01R 19/00* (2006.01)
*B82Y 15/00* (2011.01)
*G01R 1/28* (2006.01)
*G01N 27/414* (2006.01)
*G01N 27/48* (2006.01)

(52) U.S. Cl.
CPC . *B82Y 15/00* (2013.01); *G01R 1/28* (2013.01); *G01R 19/0084* (2013.01); *G01N 27/4146* (2013.01); *G01N 27/48* (2013.01); *Y10S 977/742* (2013.01)

USPC .......... 324/98; 324/76.11; 977/742

(58) Field of Classification Search
CPC .. G01R 1/28; G01R 19/0023; G01R 19/0084; G01R 19/0092; G01R 15/165; G01R 29/12; G01N 27/4146; G01N 27/48; B82Y 15/00
USPC ........ 324/76.11, 98, 425, 426, 433, 444, 522, 324/713, 72, 72.5; 340/636.1, 636.12, 340/636.15, 660; 361/79, 78; 702/64; 977/742, 842; 204/193, 194, 228.1, 204/229.4, 229.8, 230.2; 205/337, 642, 205/643, 644, 726, 727, 83, 82, 81
See application file for complete search history.

(56) References Cited

U.S. PATENT DOCUMENTS

| 6,277,255 B1 * | 8/2001 | Green et al. .................. 204/406 |
| 7,842,174 B2 * | 11/2010 | Zhou et al. .................... 204/406 |
| 2007/0236224 A1 * | 10/2007 | Augustyniak et al. ........ 324/425 |

* cited by examiner

Primary Examiner — Hoai-An D Nguyen
(74) Attorney, Agent, or Firm — Sherr & Jiang, PLLC (57) ABSTRACT

A reference potential adjusting apparatus is provided. The reference potential adjusting apparatus includes a reference potential measuring unit configured to measure a potential of a solution, a counter electrode disposed in the solution, and configured to change the potential of the solution through oxidation-reduction reactions with the solution, and a comparator configured to compare a measurement voltage provided by the reference voltage measuring unit to a reference voltage provided by a reference voltage supply unit, and to adjust reactions of the counter electrode with the solution according to the result of the comparison. The reference potential measuring unit includes a reference electrode, a common electrode disposed to be spaced apart from the reference electrode, and at least one nano structure contacting the reference electrode and the common electrode, and having electrical conductivity changing according to the potential of the solution.

23 Claims, 6 Drawing Sheets

REFERENCE POTENTIAL ADJUSTMENT DEVICE AND A MEASURING DEVICE EQUIPPED WITH THE SAME

CROSS REFERENCE TO PRIOR APPLICATIONS

This application is a National Stage Patent Application of PCT International Patent Application No. PCT/KR2011/001006(filed on Feb. 16, 2011) under 35U.S.C. §371, which claims priority to Korean Patent Application Nos. 10-2010-0028922(filed on Mar. 31, 2010) and 10-2010-0051966(filed on Jun. 1, 2010), which are all hereby incorporated by reference in their entirety.

BACKGROUND

1. Field of the Invention

The present invention relates to reference potential measurement, and more particularly, to a reference potential adjusting apparatus and a measurement apparatus including the same.

2. Discussion of Related Art

In general, an electrochemical analysis method uses a 3-electrode type measurement apparatus to analyze a material using electrodes. The 3-electrode type measurement apparatus is composed of three electrodes including a working electrode, a counter electrode, and a reference electrode. In detail, in a chemical analysis apparatus containing a solution in which oxidation-reduction reactions occur, an electrode that causes electrode reactions with a material to be measured is called a "working electrode," and an electrode whose one side has a relatively large area or is made of a high reactivity material is called a "counter electrode." Also, an electrode for monitoring the electrochemical potential of the solution to maintain the concentration in the solution constant of ions subject to the oxidation-reduction reactions is called a "reference electrode." Also, a constant potential that is measured by the reference electrode is called a "reference potential."

Figure 1:
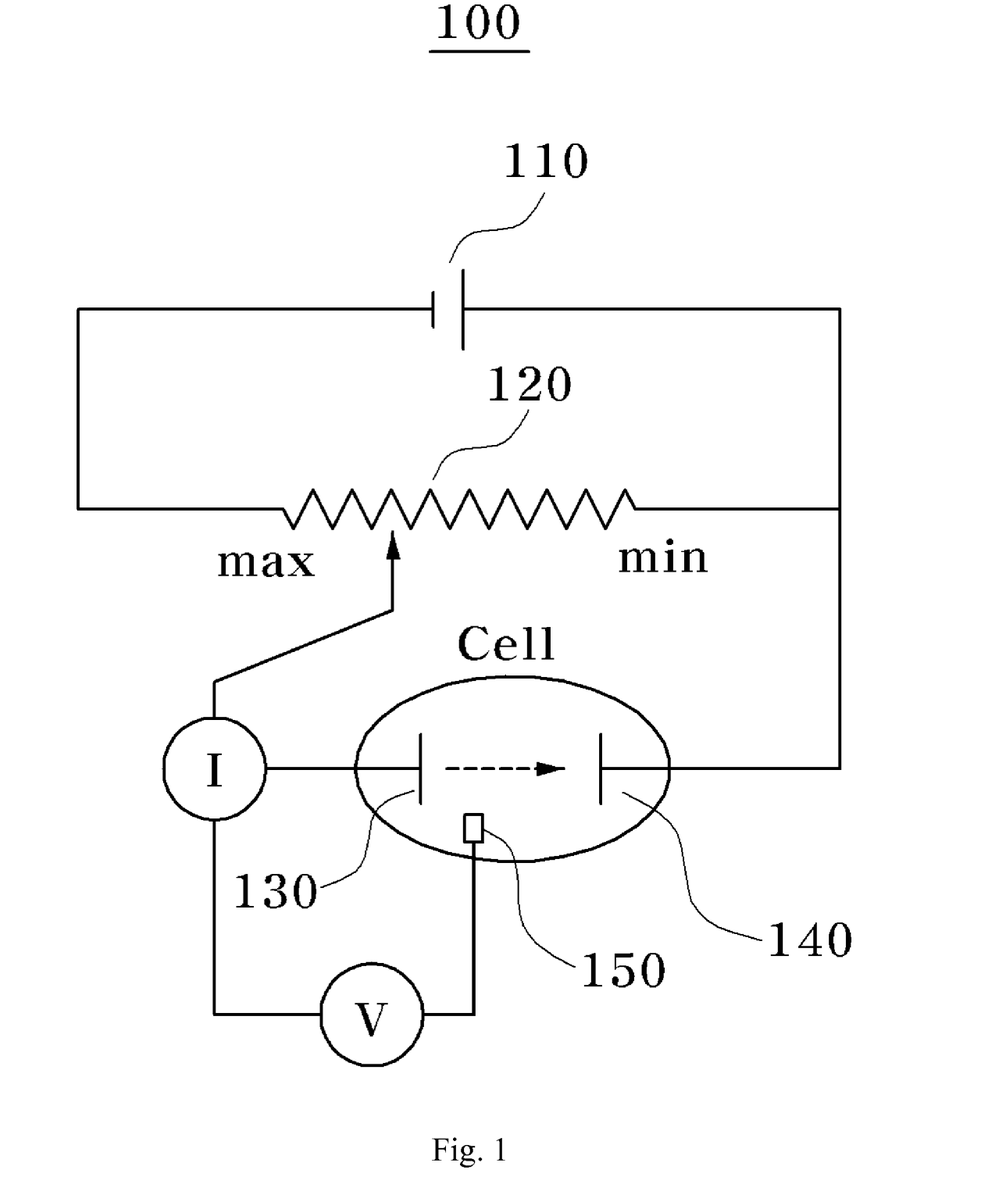
FIG. 1 is a circuit diagram illustrating a conventional 3-electrode type measurement apparatus.

FIG. 1 is a circuit diagram illustrating a conventional 3-electrode type measurement apparatus 100. Referring to FIG. 1, the 3-electrode type measurement apparatus 100 includes a voltage supply unit 110, a variable resistor 120, a working electrode 130, a counter electrode 140, and a reference electrode 150.

The reference electrode 150 is provided to measure a reference potential of the 3-electrode type measurement apparatus 100. The reference electrode 150 drives a feedback circuit based on the measured potential of a solution to change a voltage applied between the working electrode 130 and the counter electrode 140. Thereby, the reference electrode 150 can maintain a constant reference potential so that the 3-electrode type measurement system 100 can stably operate.

In the conventional 3-electrode type measurement apparatus 100, the reference electrode 150 may be a standard hydrogen electrode (SHE), a saturated calomel electrode (SCE), an Ag/AgCl electrode, a $Cu/CuSO_4$ electrode, or an Hg electrode, and the above-mentioned electrodes are made of materials capable of causing direct oxidation-reduction reactions with the solution. However, when the method of setting the reference potential using the conventional electrodes is applied to a bio sensor, etc., the following problems are generated. First, in order to manufacture a bio sensor, etc. using a semiconductor manufacturing method, an additional process for applying the above-mentioned materials is needed and also specific reaction areas should be added, which makes manufacturing of such a sensor product difficult. Second, since at least one ion in an aqueous solution should be the kind which can be oxidized or reduced to ions of a reference electrode material, the kinds of available solutions may be limited. Third, since the reference electrode is worn down due to oxidation-reduction reactions, the sensor's lifetime may be shortened. Fourth, the sensor may be sensitive to environmental factors such as temperature.

Accordingly, demands for an improved measurement apparatus capable of stabilizing a measurement system by easily setting a reference potential without causing the above-described problems are increasing.

Also, many sensors that are driven in a solution such as an electrolyte, other than the 3-electrode type measurement apparatus, require a stable operation environment and a more reliable apparatus for controlling a reference potential.

SUMMARY OF THE INVENTION

The present invention is directed to a reference potential adjusting apparatus including an improved reference potential measuring unit for setting a reference potential for a solution and measuring it.

The present invention is also directed to a measurement apparatus to which a reference potential adjusting apparatus including a reference potential measuring unit is applied.

According to an aspect of the present invention, there is provided a reference potential adjusting apparatus. The reference potential adjusting apparatus includes a reference potential measuring unit configured to measure a potential of a solution, a counter electrode disposed in the solution, and configured to change the potential of the solution through oxidation-reduction reactions with the solution, and a comparator configured to compare a measurement voltage provided by the reference voltage measuring unit to a reference voltage provided by a reference voltage supply unit, and to adjust reactions of the counter electrode with the solution according to the result of the comparison. The reference potential measuring unit includes a reference electrode, a common electrode disposed to be spaced apart from the reference electrode, and at least one nano structure contacting the reference electrode and the common electrode, and having electrical conductivity changing according to the potential of the solution.

According to another aspect of the present invention, there is provided a 3-electrode type measurement apparatus. The 3-electrode type measurement apparatus includes a working electrode configured to cause electrode reactions of an object to be analyzed in a solution, a counter electrode disposed to face the working electrode, a reference potential measuring unit configured to measure a potential of the solution, and a comparator configured to compare a measurement voltage provided by the reference potential to a reference voltage provided by a reference voltage supply unit, and to adjust reactions of the counter electrode with the solution according to the result of the comparison. The reference potential measuring unit includes a field effect device configured to change conductivity of charges flowing through the reference potential measuring unit according to the potential of the solution.

According to another aspect of the present invention, there is provided a sensor. The sensor includes a sensing apparatus and a reference potential adjusting apparatus. The sensing apparatus includes a first electrode disposed on a substrate, a second electrode spaced apart from the first electrode, and at least one nano structure contacting the first electrode and the second electrode, and having electrical characteristics changing according to an object to be sensed in a solution. The reference potential adjusting apparatus includes a counter electrode disposed in the solution, and configured to change a potential of the solution through oxidation-reduction reactions with the solution, a reference potential measuring unit configured to measure the potential of the solution, and a comparator configured to compare a measurement voltage provided by the reference potential measuring unit to a reference voltage provided by a reference voltage supply unit, and to generate a control signal for adjusting reactions of the counter electrode with the solution according to the result of the comparison, the comparator including a field effect device configured to change conductivity of charges flowing through the reference potential measuring unit according to the potential of the solution.

Therefore, according to the embodiments as described above, it is possible to replace a conventional reference electrode made of Ag or AgCl with a reference potential measuring unit made of a material such as carbon nanotubes (CNTs) or graphene whose electrical conductivity changes sensitively according to the potential of a solution. The measurement apparatus and the sensor including the measurement apparatus, according to the embodiments as described above, can be implemented to have simple structures, and also manufactured through a simplified manufacturing process, compared to a conventional measurement apparatus using a material such as Ag or AgCl for a reference electrode and a sensor including the conventional measurement apparatus. Accordingly, a cost of fabricating a structure for measuring a reference potential can be reduced. Consequently, through a simplified structure of a reference potential measuring apparatus, high economic efficiency can be achieved in view of yield.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Various embodiments will now be described more fully with reference to the accompanying drawings in which some embodiments are shown. These present inventions may, however, be embodied in different forms and should not be construed as limited to the embodiments set forth herein. Rather, these embodiments are provided so that this disclosure is thorough and complete and fully conveys the present invention to those skilled in the art. In the drawings, the sizes and relative sizes of layers and regions may be exaggerated for clarity.

The terminology used herein is for the purpose of describing particular embodiments only and is not intended to be limiting of the present invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this present invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Figure 2:
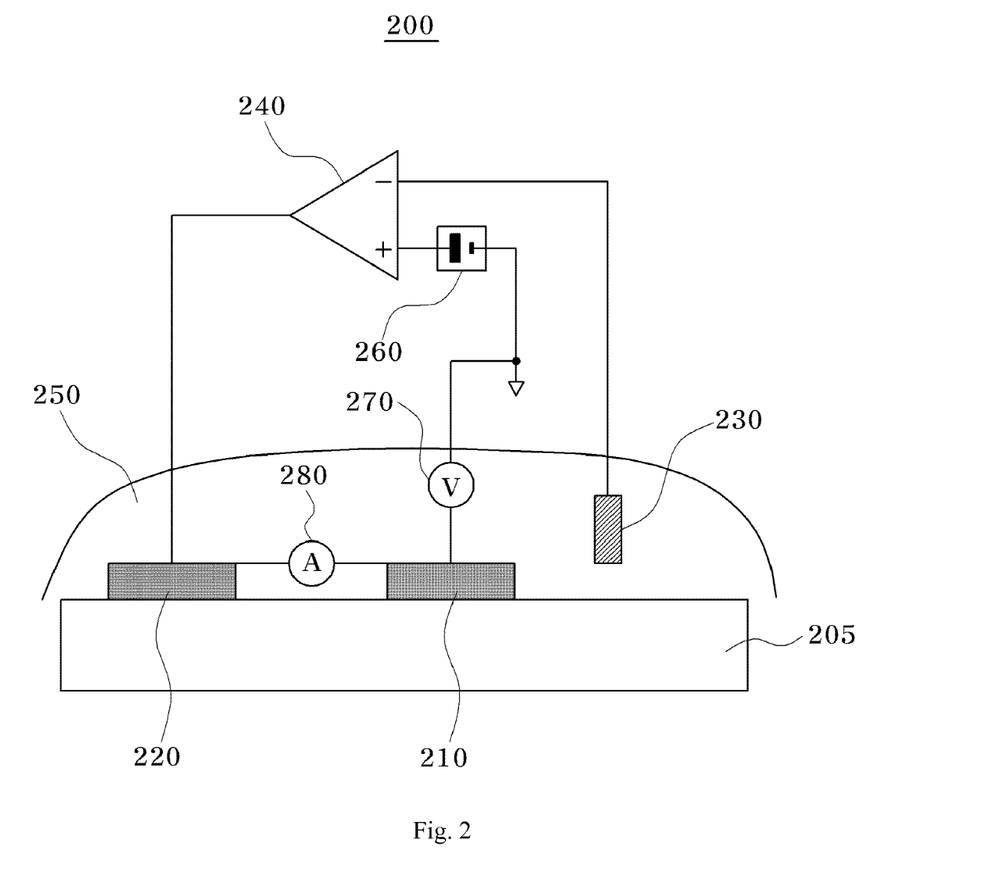
FIG. 2 is a diagram illustrating a measurement apparatus according to a comparative example of the present invention.

FIG. 2 is a diagram illustrating a measurement apparatus 200 according to a comparative example of the present invention. Although the comparative example illustrated in FIG. 2 is designed and proposed by the present applicant, the measurement apparatus illustrated in FIG. 2 is different from a measurement apparatus according to an embodiment of the present invention. A method of measuring a reference potential using the measurement apparatus illustrated in FIG. 2 can be used as a comparative means to help with understanding of the embodiments of the present invention, which will be described later with reference to FIGS. 3 through 6.

Referring to FIG. 2, the measurement apparatus 200 is a 3-electrode type measurement apparatus, and includes a working electrode 210, a counter electrode 220, a reference electrode 230, and a comparator 240. The working electrode 210 and the counter electrode 220 are placed on a substrate 205, the reference electrode 230 is positioned in a solution 250, and the comparator 240 is spaced apart from the working electrode 210, the counter electrode 220, and the reference electrode 230. The working electrode 210 causes a material to be analyzed to undergo electrode reactions with the solution 250. The reference electrode 230 measures the solution potential of the solution 250. The reference electrode 230 may be made of a material such as Ag or AgCl in order to produce a current through oxidation-reduction reactions with the solution 250. For example, the solution potential of an electrolyte solution to be measured may be input to the negative (−) input terminal of the comparator 240. A predetermined reference voltage from a reference voltage supply unit 260 may be input to the positive (+) input terminal of the comparator 240. The comparator 240 amplifies a difference between the solution potential and the reference voltage, and sends the result of the amplification as a control signal to the counter electrode 220. The control signal may be an amplified voltage signal. In this case, the control signal is used to adjust oxidation-reduction reactions of the counter electrode 220 with the solution 250. That is, if the solution potential measured by the reference electrode 230 is lower than the predetermined reference voltage, the control signal facilitates oxidation-reduction reactions of the counter electrode 220 with the solution 250 to raise the solution potential, and if the solution potential is higher than the predetermined reference voltage, the control signal impedes oxidation-reduction reactions of the counter electrode 220 with the solution 250 to lower the solution potential. As such, by controlling electrochemical reactions of the counter electrode 220 with the solution 250, it is possible to equalize the solution potential to the predetermined reference voltage.

When the solution potential is maintained to be equalized to the predetermined reference voltage, a predetermined driving voltage supplied from a separate driving voltage supply unit 270 is applied between the working electrode 210 and the counter electrode 220, and electrical measurement with respect to electrochemical reactions occurring between the working electrode 210 and the solution 250 is performed. Thereby, it is possible to measure a driving potential at the working electrode 210 in the 3-electrode type measurement apparatus 200. When the driving voltage is supplied, the solution potential may again change due to electrode reactions between the working electrode 210 and the solution 250. According to an example, by designing the 3-electrode type measurement apparatus 200 such that an oxidation-reduction current between the counter electrode 220 and the solution 250 is higher than an oxidation-reduction current between the working electrode 210 and the solution 250, it is possible to measure only the driving potential between the working electrode 210 and the solution 250 while maintaining the solution potential constant. Accordingly, by measuring an electrical parameter such as a current due to the driving potential through a measurer 280 disposed between the working electrode 210 and the counter electrode 220, it is possible to recognize oxidation-reduction characteristics of the working electrode 210.

In the comparative example described above, the reference electrode 230 made of a well-known material such as Ag or AgCl may have problems when it is used in a bio sensor, etc. First, in order to manufacture a bio sensor, etc. using a semiconductor manufacturing method, an additional process for applying the material such as Ag or AgCl is needed and also reaction areas in which Ag or AgCl contacts a solution should be separately manufactured. Second, since at least one ion in an aqueous solution should be the kind which can be oxidized or reduced to ions of a reference electrode material, the kinds of available solutions may be limited. Third, since the reference electrode is worn down due to oxidation-reduction reactions, the sensor's lifespan may be shortened. Fourth, the sensor may be sensitive to environmental factors such as temperature. Hereinafter, an embodiment of the present invention configured to overcome the problems will be described.

Figure 3:
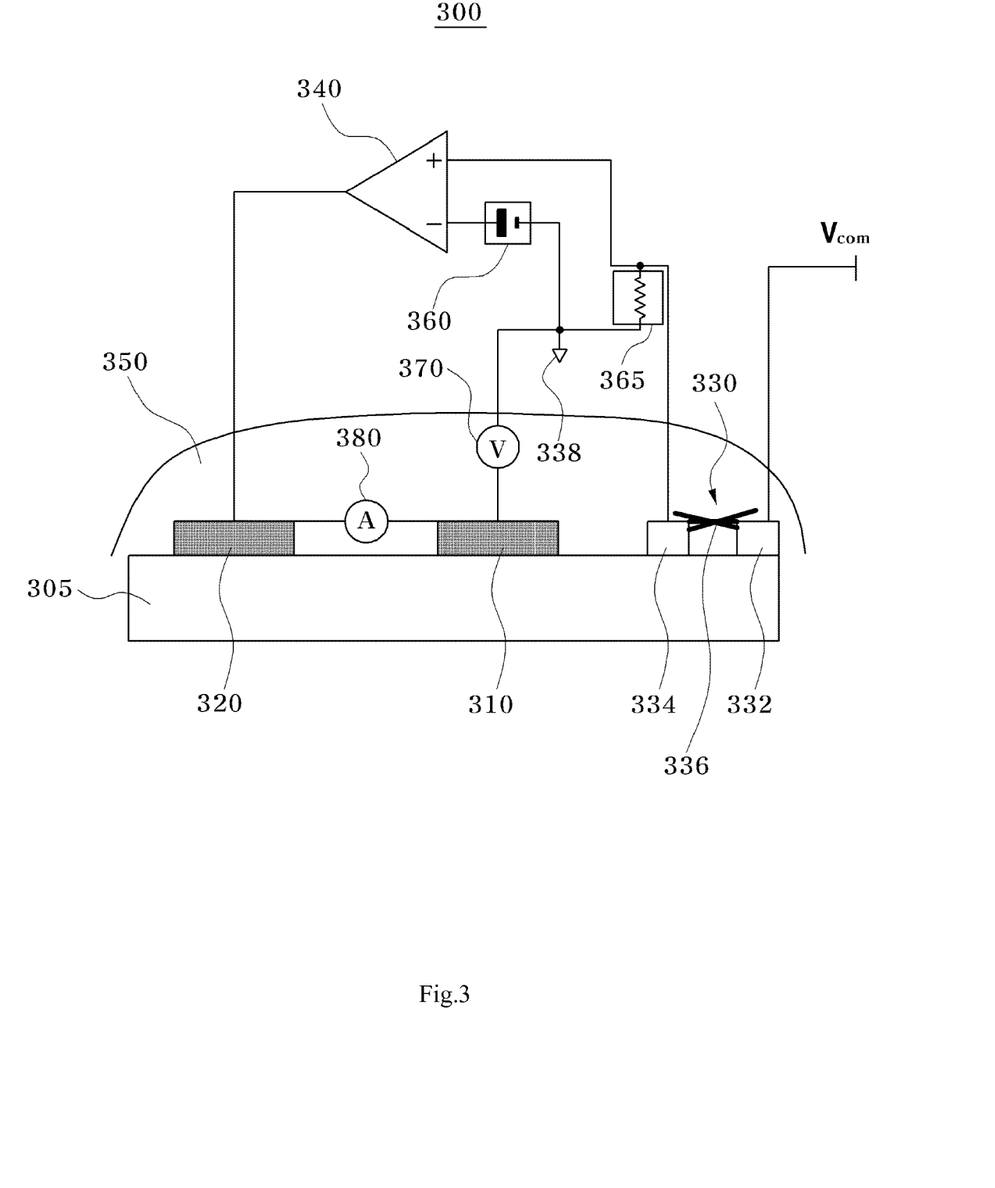
FIG. 3 is a diagram illustrating a measurement apparatus according to an embodiment of the present invention.

FIG. 3 is a diagram illustrating a measurement apparatus 300 according to an embodiment of the present invention. Referring to FIG. 3, the measurement apparatus 300 is a 3-electrode type measurement apparatus, and includes a reference potential measuring unit that functions as a reference electrode. The reference potential measuring unit may include a field effect device. That is, the 3-electrode type measurement apparatus 300 illustrated in FIG. 3 is different from the 3-electrode type measurement apparatus 200 illustrated in FIG. 2 in that the reference potential measuring unit includes a field effect device. The field effect device may be a field effect transistor (FET). In the field effect device such as the FET, the conductivity of charges moving across the channel layer between the source electrode and the drain electrode may change according to the potential of the gate electrode. In the current embodiment, based on the characteristics, the electrochemical potential of the solution acts as a gate voltage applied to the gate electrode, and when a current value between the source electrode and the drain electrode is changed, the changed current is measured to monitor the potential of the solution. Also, by controlling oxidation-reduction reactions between the electrode and the solution based on the monitored potential of the solution, it is possible to maintain the potential of the solution constant. The present inventor uses a nano structure having excellent sensitivity to the electrochemical potential of a solution, compared to general semiconductor materials, to measure a reference potential. The nano structure may be at least one selected from the group consisting of a metal having electrical conductivity, a metal oxide, a semiconductor, and a conductive polymer. For example, the nano structure may be made of a carbon nanotube (CNT) or graphene. As another example, the nano structure may be a semiconductor nanowire. The semiconductor nanowire may be made of $SnO_2$, $ZnO_2$, $In_2O_3$, or CdO. The nano structure may be in the shape of a nanotube, a nanowire, a nanorod, a nanoribbon, a nanofilm, or a nanoball.

Referring to FIG. 3, the measurement apparatus 300 includes a working electrode 310, a counter electrode 320, a reference potential measuring unit 330, and a comparator 340. Also, the measurement apparatus 300 may include a reference voltage supply unit 360, a voltage converter 365, and a driving voltage supply unit 370. In the measurement apparatus 300, the working electrode 310, the counter electrode 320, and the reference potential measuring unit 330 may be arranged on a substrate 305. The working electrode 310 causes electrode reactions of a material to be analyzed in the solution 350. The counter electrode 320 is disposed to face the working electrode 310 on the substrate 305. The counter electrode 320 may undergo oxidation-reduction reactions with the solution 350 under the control of the comparator 340. The comparator 340 may be an operational amplifier. The solution potential of the solution 350 may be adjusted by means of the comparator 340. The counter electrode 320 maintains a driving voltage with respect to the working electrode 310, thereby causing electrode reactions between the working electrode 310 and the solution 350.

The reference potential measuring unit 330 may include a field effect device that functions to change the conductivity of charges flowing through the reference potential measuring unit 330 according to the magnitude of the solution potential of the solution 350. The reference potential measuring unit 330 may include a reference electrode 334, a common electrode 332, and a channel layer 336 disposed between the reference electrode 334 and the common electrode 332. According to an example, the reference electrode 334 may function as the source electrode of the field effect device, and the common electrode 332 may function as the drain electrode of the field effect device, according to the flow of charges. Alternatively, the reference electrode 334 may function as the drain electrode of the field effect device, and the common electrode 332 may function as the source electrode of the field effect device. The channel layer 336 may be made of a material whose electrical conductivity changes sensitively according to the solution potential. For example, the channel layer 336 may be made of CNTs or graphene. The common electrode 332 may be connected to a common voltage supply unit $V_{com}$, and the reference electrode 334 may be connected to the voltage converter 365.

According to an example, the field effect device may operate as a FET. In this case, the solution potential of the solution 350 may act as a gate voltage that is applied to the FET. In detail, the channel layer 336 made of CNTs or graphene contacts the solution 350, and the conductivity of charges moving from the common electrode 332 to the reference electrode 334 through the CNTs or graphene changes according to the magnitude of the solution potential. The flow (that is, a current) of the charges output from the reference electrode 334 may be input to the voltage converter 365. The voltage converter 365 converts the current changing according to a change of the solution potential into a measurement voltage. That is, the voltage converter 365 functions to convert the current into the measurement voltage, and may be implemented in various circuit techniques. For example, the voltage converter 365 includes a converter resistor to calculate the measurement voltage based on a ratio of the resistance value of the channel layer 336 to the resistance value of the converter resistor, and output the measurement voltage. The measurement voltage output from the voltage converter 365 is input to an input terminal of the comparator 340. As such, the reference potential measuring unit 330 calculates the solution potential of the solution 350 as the measurement voltage, and provides the measurement voltage to the comparator 340. The other input terminal of the comparator 340 receives a predetermined reference voltage from the reference voltage supply unit 360.

According to an example, the conductance modulation device depending on the chemical potential of aqueous solution (the reference potential measuring unit 330) may show the characteristics of a P-type field effect transistor, and in this case, the voltage converter 365 may be disposed between a ground 338 and the drain electrode (that is, the reference electrode 334) of the P-type field effect transistor. The potential of the reference electrode 334 may change according to a change of the solution potential. The potential of the reference electrode 334 is converted into the measurement voltage according to the ratio of the resistance value of the channel layer 336 to the resistance value of the converter resistor, and then input to the positive (+) input terminal of the comparator 340. Meanwhile, the negative (−) input terminal of the comparator 340 receives the predetermined reference voltage from the reference voltage supply unit 360.

The comparator 340 may be an operational amplifier. The comparator 340 may amplify a difference between the measurement voltage and the reference voltage, and sends the result of the amplification as a control signal to the counter electrode 320. The control signal may be a predetermined voltage for adjusting a degree of oxidation-reduction reactions occurring between the counter electrode 320 and the solution 350. The magnitude of the predetermined voltage may depend on the amplification characteristic of the comparator 340. According to an example, the comparator 340 compares the measurement voltage to the reference voltage. If the measurement voltage is lower than the reference voltage, the comparator 340 may generate a control signal for facilitating oxidation-reduction reactions of the counter electrode 320 with the solution 350 to raise the solution potential of the solution 350. Meanwhile, if the measurement voltage is higher than the reference voltage, the comparator 340 may generate a control signal for impeding oxidation-reduction reactions of the counter electrode 320 with the solution 350 to lower the solution potential of the solution 350.

By controlling oxidation-reduction reactions through a feedback mechanism as described above, the solution potential is adjusted to be equalized to the reference potential designated by the reference voltage. When the solution potential is adjusted to be equalized to the reference potential, the predetermined driving voltage from the driving voltage supply unit 370 is applied between the working electrode 310 and the counter electrode 350, and electrical measurement on electrochemical reactions occurring between the working electrode 310 and the solution 350 is performed. Thereby, it is possible to measure a driving potential at the working electrode 310 in the 3-electrode type measurement apparatus. When the driving voltage is applied, the solution potential may again change due to electrode reactions occurring between the working electrode 310 and the solution 350. According to an example, by designing the 3-electrode type measurement apparatus 300 such that an oxidation-reduction current between the counter electrode 320 and the solution 350 is higher than an oxidation-reduction current between the working electrode 310 and the solution 350, it is possible to measure only the driving potential between the working electrode 310 and the solution 350 while maintaining the solution potential constant. For example, by measuring an electrical parameter such as a current due to the driving potential through a measurer 380 disposed between the working electrode 310 and the counter electrode 320, it is possible to recognize oxidation-reduction characteristics of the working electrode 310.

Figure 4:
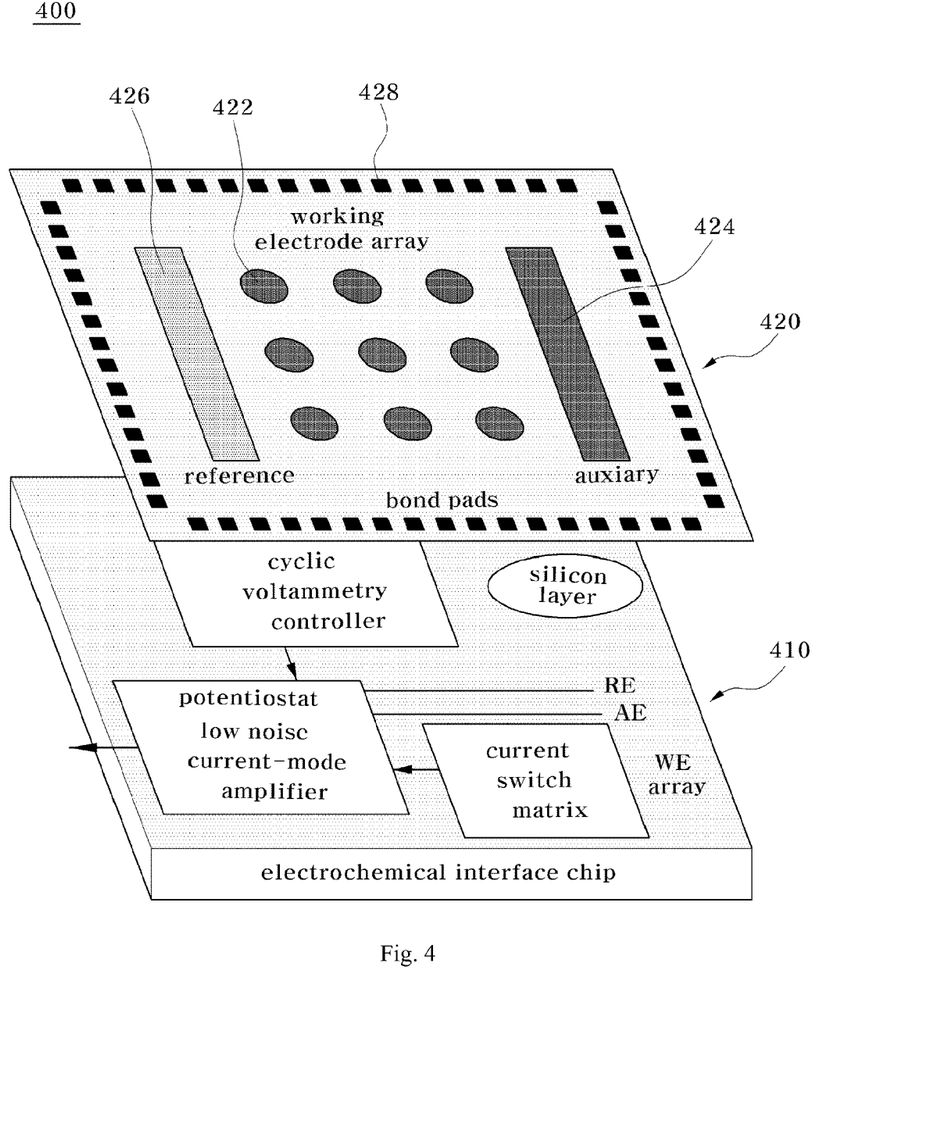
FIG. 4 is a diagram illustrating a sensor including the measurement apparatus illustrated in FIG. 3, according to an embodiment of the present invention.

FIG. 4 is a diagram illustrating a sensor 400 including the measurement apparatus illustrated in FIG. 3, according to an embodiment of the present invention. Referring to FIG. 4, the sensor 400 may have a layered structure consisting of two layers: a lower layer 410 and an upper layer 420. The lower layer 410 may be implemented as a semiconductor chip, and include a control circuit, an amplifier, a switch, etc., wherein the control circuit and the amplifier are used to operate the upper layer 420, and the switch is used to select, when a working electrode array is used, a working electrode from the working electrode array. The upper layer 420 may be implemented as an electrode structure connected to the lower structure 410, and include a plurality of working electrodes 422, a counter electrode 424, and a reference potential measuring unit 426, and a pad 428, wherein the working electrodes 422 contact a solution, and the pad 428 is used to connect the sensor 400 to an external device. The solution potential should be monitored by the reference potential measuring unit 426 so that the solution potential can be maintained constant before electrode reactions occur between the solution and the working electrodes 422. The solution potential can be maintained constant through the feedback mechanism of the 3-electrode type measurement apparatus.

Figure 5:
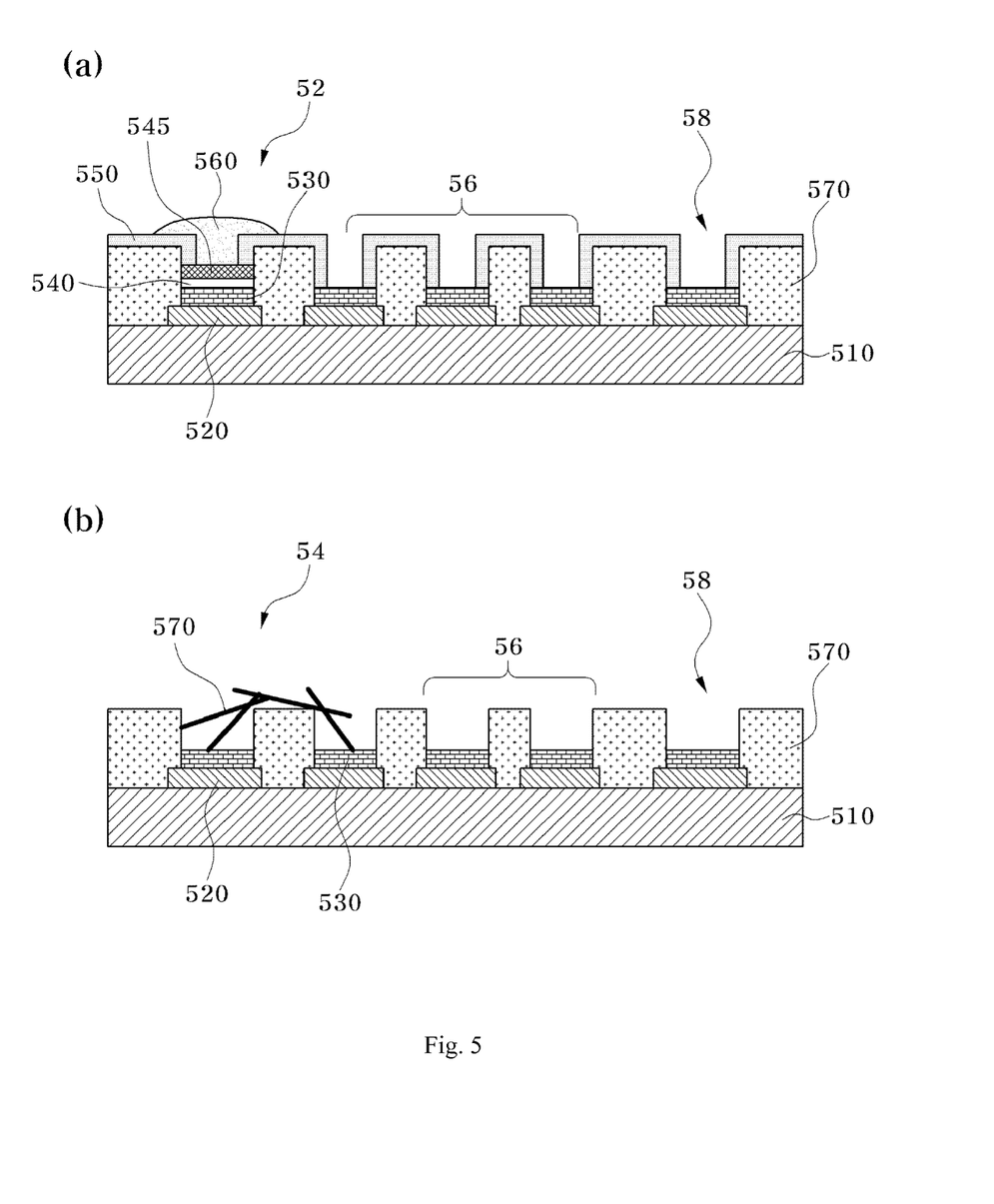
FIG. 5 is a cross-sectional view of a sensor including the measurement apparatus illustrated in FIG. 3, according to an embodiment of the present invention.

FIG. 5 is a cross-sectional view of the sensor 400 including the measurement apparatus 300 illustrated in FIG. 3, according to an embodiment of the present invention. In detail, FIG. 5 shows an example of the upper layer 420 of the sensor 400 illustrated in FIG. 4. (a) of FIG. 5 shows a comparative example in which an Ag or AgCl electrode is used as a reference electrode 52, and (b) of FIG. 5 shows an example in which a reference potential measuring unit 54 functions as a reference electrode. The reference potential measuring unit 54 may be a field effect device using a channel layer.

Referring to (a) of FIG. 5, the reference electrode 52 has a laminate structure that is different from that of working electrodes 56 or a counter electrode 58. The reference electrode 52 includes an electrode layer 530 formed on a support layer of a substrate 510, a Ag layer 540 formed on the electrode layer 530, a AgCl layer 545 formed on the Ag layer 540, and a Nafion layer 560 formed on the AgCl layer 545. The Nafion layer 500 acts as an ion permeable layer. The electrode layer 530 may have a laminate structure made of titanium or gold. Spin-on-glass layers 550 and insulation layers 570 function to isolate the working electrodes 56, the counter electrode 58, and the reference electrode 52 from one another.

Referring to (b) of FIG. 5, the reference potential measuring unit 54 includes a plurality of electrode layers 530 respectively formed on support layers of a substrate 510, and a plurality of channel layers 570 arranged in correspondence to the respective electrode layers 530. According to an example, the channel layers 570 may be made of CNTs or graphene. As described above, the channel layers 570 may change the conductivity of moving charges according to the magnitude of the solution potential of a solution in which the sensor 400 is driven. In the reference potential measuring unit 54, one of the neighboring electrode layers 530 may function as a source electrode, and the other may function as a drain electrode.

Comparing (a) of FIG. 5 to (b) of FIG. 5, since the reference potential measuring unit 54 includes a field effect device made of a material, such as CNTs or graphene, sensitive to a solution potential, the reference potential measuring unit 54 may have a simpler structure than the reference electrode 52 provided as a comparative example. That is, since the reference potential measuring unit 54 has a simple structure, the manufacturing process of the sensor 400 can be simplified, and accordingly, a manufacturing cost can also be reduced.

Figure 6:
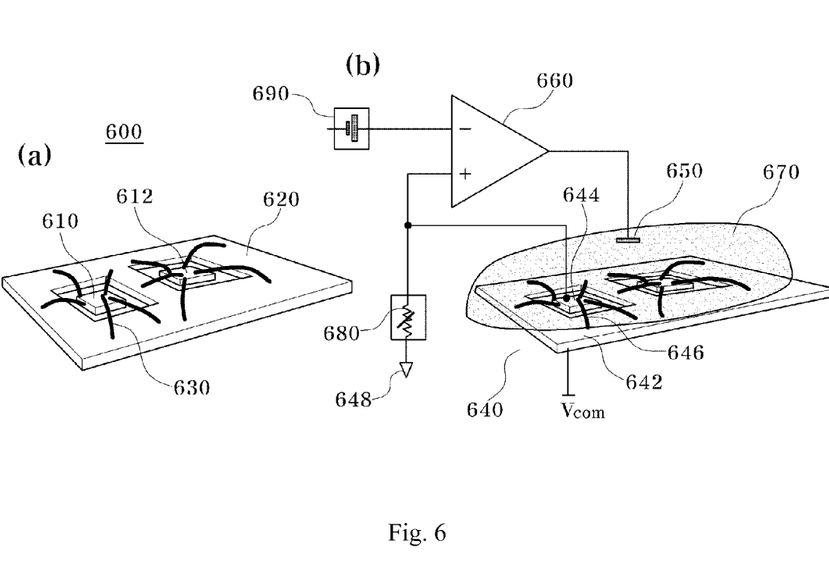
FIG. 6 is a diagram illustrating a sensor according to another embodiment of the present invention.

FIG. 6 is a diagram illustrating a sensor 600 according to another embodiment of the present invention. An adjusting apparatus for controlling a reference potential of a solution using the field effect device of the measurement apparatus 300 or 400 illustrated in FIG. 3, 4, or 5 can be applied to various kinds of sensors. The sensor 600 may include a sensing apparatus and a reference potential adjusting apparatus. (a) of FIG. 6 shows the sensing apparatus of the sensor 600, and (b) of FIG. 6 shows the reference potential adjusting apparatus of the sensor 600, wherein the reference potential adjusting apparatus includes a measurement apparatus according to an embodiment of the present invention.

Referring to (a) of FIG. 6, the sensing apparatus of the sensor 600 includes first electrodes 610 and 620, a second electrode 620 spaced apart from the first electrodes 610 and 620, and at least one nano structure 630 that contacts the first electrodes 610 and 620 and the second electrode 610. The first electrodes 610 and 612 are disposed to be physically isolated from the second electrode 620. The nano structure 630 may electrically connect the first electrodes 610 and 612 to the second electrode 620. The nano structure 630 may be made of at least one selected from the group consisting of a metal having electrical conductivity, a metal oxide, a semiconductor, and a conductive polymer. For example, the nano structure 630 may be made of a CNT or graphene. As another example, the nano structure 630 may be a semiconductor nanowire. The semiconductor nanowire may be made of $SnO_2$, $ZnO_2$, $In_2O_3$, or CdO. The nano structure 630 may be in the shape of a nanotube, a nanowire, a nanorod, a nanoribbon, a nanofilm, or a nanoball.

As illustrated in (a) of FIG. 6, the second electrode 620 may be disposed to surround the first electrodes 610 and 612, and the second electrode 620 may influence both of the first electrodes 610 and 612. The sensing apparatus of the sensor 600 may be a field effect transistor. In this case, the first electrodes 610 and 612 may act as the source electrode of the field effect transistor, and the second electrode 620 may act as the drain electrode of the field effect transistor. On the other hand, it is also possible for the second electrode 620 to act as the source electrode of the field effect transistor, and the first electrode 610 to act as the drain electrode of the field effect transistor.

The nano structure 630 functions as the channel layer of the field effect transistor. The electrical characteristics of the nano structure 630 change according to whether or not an object to be sensed by the sensor 600 exists or according to the concentration of the object to be sensed by the sensor 600. The electrical characteristics of the nano structure 630 may be electrical conductivity or resistance. The object to be sensed by the sensor 600 may be a protein, DNA, molecules, or ions. The nano structure 630 may be treated to react to a specific object. For example, the nano structure 630 may be coupled with a receptor reacting to a specific protein, tumor marker, molecule, or virus in a solution.

According to an example, in a sensing apparatus of a sensor, a device including a first electrode and a second electrode surrounding the first electrode may be classified as a unit sensor. Referring to (a) of FIG. 6, the sensing apparatus may be composed of two unit sensors: one including the first electrode 610 and the second electrode part 620 surrounding the first electrode 610, and the other including the first electrode 612 and the second electrode part 620 surrounding the first electrode 612.

According to another example, in a sensing apparatus of a sensor, a device including two first electrodes and a second electrode surrounding the first electrodes may be classified as a unit sensor. Referring to (a) of FIG. 6, the sensing apparatus may be composed of a single unit sensor including two first electrodes 610 and 620 and a second electrode 620 surrounding the first electrodes 610 and 612. In this case, the sensing apparatus of the unit sensor may be composed of an adjusting device including the first electrode 610 and the second electrode part 620 surrounding the first electrode 610, and a sensing device including the first electrode 612 and the second electrode part 620 surrounding the first electrode 612. According to an example, the nano structure 630 in the sensing device is coupled with a receptor reacting to an object to be sensed, and the nano structure 630 in the adjusting device is not coupled with any receptor or is coupled with a receptor having different characteristics. Generally, the sensor 600 operates using characteristics in which the electrical characteristics of the nano structure 630 change by specific binding between the receptor and the object to be sensed. However, when the sensor 600 operates, abnormal noise signals may be generated. For example, nonspecific binding between the nano structure 630 and the object to be sensed may occur, that is, the object to be sensed may be coupled with a portion of the nano structure 630 other than the receptor. In this case, the electrical characteristics of the nano structure 630 change, resulting in generation of a noise signal. When the sensing apparatus includes both the adjusting device and the sensing device, by detecting a noise signal due to such nonspecific binding and reflecting the results of the detection to a signal detected by the detecting device, it is possible to filter only electrical signals generated by specific binding, while contributing to reliability improvement of the sensor 600.

When the object to be sensed by the sensor 600 is provided through a solution, it is necessary to maintain the potential of the solution constant while the sensor 600 operates. For maintaining the potential of the solution constant, the sensor 600 provides the reference potential adjusting apparatus. Referring to (b) of FIG. 6, the reference potential adjusting apparatus of the sensor 600 uses an electrode selected from the first electrode 610 and the second electrode 620 as a reference potential measuring unit 640, thereby measuring a reference potential in a solution. The reference potential adjusting apparatus of the sensor 600 includes the reference potential measuring unit 640, a counter electrode 650, and a comparator 660. The comparator 660 may be an operational amplifier.

The reference potential measuring unit 640 includes a field effect device that functions to change the conductivity of charges flowing through a nano structure electrode 646 (also, referred to as a channel layer) according to the magnitude of the solution potential of a solution 670. The reference potential measuring unit 640 may include a reference electrode 644, a common electrode 642, and a channel layer 646 disposed between the reference electrode 644 and the common electrode 642. According to an example, the reference electrode 644 may function as the source electrode of the field effect device, and the common electrode 642 may function as the drain electrode of the field effect device, according to the flow of charges. Alternatively, it is also possible for the reference electrode 644 to function as the drain electrode of the field effect device, and the common electrode 642 to function as the source electrode of the field effect device.

The common electrode 642 may be connected to a common voltage supply unit $V_{com}$, and the reference electrode 644 may be connected to a voltage converter 680. The channel layer 646 may be made of a material whose electrical conductivity changes sensitively according to the solution potential. The material may be CNTs or graphene. According to an example, the common electrode 642, the reference electrode 644, and the channel layer 646 may correspond to the second electrode 620, the first electrodes 610 and 612, and the nano structure 630, respectively. According to an example, the field effect device may be a field effect transistor.

In this case, the solution potential of the solution 670 may act as a gate voltage applied to the field effect transistor. In detail, the channel layer 646 made of CNTs or graphene contacts the solution 670, and the conductivity of charges moving from the common electrode 642 to the reference electrode 644 through the channel layers 646 changes according to the magnitude of the solution potential of the solution 670. The flow (that is, a current) of the charges output from the reference electrode 644 may be converted into a measurement voltage by the voltage converter 680. That is, the voltage converter 680 functions to convert the current into the measurement voltage, and may be implemented in various circuit techniques. For example, the voltage converter 680 includes a converter resistor to create the measurement voltage based on a ratio of the resistance value of the channel layer 646 to the resistance value of the converter resistor. The measurement voltage created by the voltage converter 680 is input to an input terminal of the comparator 660. As such, the reference electrode 644 calculates the solution potential of the solution 670 as the measurement voltage, and provides the measurement voltage to the comparator 660. The other input terminal of the comparator 660 receives a predetermined reference voltage from a reference voltage supply unit 690.

According to an example, the field effect device may show the characteristics of a P-type field effect transistor, and in this case, the voltage converter 680 may be disposed between a ground 648 and the drain electrode (that is, the reference electrode 644) of the P-type field effect transistor. The potential of the reference electrode 644 may change according to a change of the solution potential. The potential of the reference electrode 644 is converted into the measurement voltage according to the ratio of the resistance value of the channel layers 646 to the resistance value of the converter resistor, and then input to the positive (+) input terminal of the comparator 660. Meanwhile, the negative (−) input terminal of the comparator 660 receives the predetermined reference voltage from the reference voltage supply unit 690.

The comparator 690 amplifies a difference between the measurement voltage and the reference voltage, and sends the result of the amplification as a control signal to the counter electrode 650. The control signal may be a predetermined voltage for adjusting oxidation-reduction reactions between the counter electrode 650 and the solution 670. The magnitude of the predetermined voltage may be decided according to the amplification characteristics of the comparator 660. According to an example, the comparator 660 compares the measurement voltage to the reference voltage. If the measurement voltage is lower than the reference voltage, the comparator 660 may generate a control signal for facilitating oxidation-reduction reactions of the counter electrode 650 with the solution 670 to raise the solution potential of the solution 670. Meanwhile, if the measurement voltage is higher than the reference voltage, the comparator 660 may generate a control signal for impeding oxidation-reduction reactions of the counter electrode 650 with the solution 670 to lower the solution potential of the solution 670.

In this way, by controlling oxidation-reduction reactions through a feedback mechanism as described above, the solution potential is adjusted to be equalized to the reference potential designated by the reference voltage. After the solution potential is adjusted to be equalized to the reference potential, the sensor 600 may perform a sensing operation. A predetermined voltage is applied between the first electrodes 610 and 612 and the second electrode 620 so that specific binding between the nano structure 630 and the object to be sensed occurs, and accordingly, the electrical characteristics of the nano structure 630 change. By detecting the change of the electrical characteristics of the nano structure 630, the sensor 600 may sense the existence and concentration of the object to be sensed.

According to some examples, the sensing apparatus and the reference potential adjusting apparatus may be configured in various structures. For example, one of the first electrodes 610 and 612 and the second electrode 620 is configured as the common electrode 642, and another one of the first electrodes 610 and 612 and the second electrode 620 is configured as the reference electrode 644. Also, the nano structure 630 of the sensing apparatus may be configured as the channel layer 646. For example, the reference potential measuring unit of the reference potential adjusting apparatus may be configured using the adjusting device of the sensing apparatus. Also, the sensing apparatus may be configured in an array structure in order to simultaneously sense various kinds of materials. Thereby, it is possible to increase a degree of integration of the sensor 600 and reduce a manufacturing cost, compared to when the reference potential adjusting apparatus and the sensing apparatus are separately manufactured.

According to some examples, the sensing apparatus of the sensor 600 may be configured to have various well-known shapes and structures, and the reference potential adjusting apparatus of the sensor 600 may be configured to have the structure described above with reference to FIG. 6.

It will be apparent to those skilled in the art that various modifications can be made to the above-described exemplary embodiments of the present invention without departing from the spirit or scope of the invention. Thus, it is intended that the present invention covers all such modifications provided they come within the scope of the appended claims and their equivalents.

What is claimed is:

1. A reference potential adjusting apparatus comprising:
a reference potential measuring unit configured to measure a potential of a solution;
a counter electrode disposed in the solution, and configured to change the potential of the solution by oxidation-reduction reactions with the solution; and
a comparator configured to compare a measurement voltage provided by the reference potential measuring unit to a reference voltage provided by a reference voltage supply unit, and to adjust reactions of the counter electrode with the solution according to the result of the comparison,
wherein the reference potential measuring unit comprises:
a reference electrode;
a common electrode disposed to be spaced apart from the reference electrode; and
at least one nano structure contacting the reference electrode and the common electrode, and having electrical conductivity changing according to the potential of the solution.

2. The reference potential adjusting apparatus of claim 1, wherein the nano structure includes at least one selected from the group consisting of a metal, a metal oxide, a semiconductor, and a conductive polymer.

3. The reference potential adjusting apparatus of claim 2, wherein the nano structure includes a carbon nanotube (CNT) or graphene.

4. The reference potential adjusting apparatus of claim 1, wherein the nano structure has a shape selected from the group consisting of a nanotube, a nanowire, a nanorod, a nanoribbon, a nanofilm, and a nanoball.

5. The reference potential adjusting apparatus of claim 1, further comprising a voltage converter connected to an input terminal of the comparator, and configured to provide the measurement voltage that is calculated in correspondence to an amount of charges flowing through the at least one nano structure of the reference potential measuring unit.

6. The reference potential adjusting apparatus of claim 5, wherein the voltage converter includes a voltage converter resistor, and creates the measurement voltage from the amount of charges, based on a resistance value of the voltage converter resistor and a resistance value of the nano structure resistor whose resistance changes according to the potential of the solution.

7. The reference potential adjusting apparatus of claim 1, wherein the comparator compares the measurement voltage to the reference voltage,
adjusts reactions of the counter electrode with the solution to raise the potential of the solution if the measurement voltage is lower than the reference voltage, and
adjusts reactions of the counter electrode with the solution to lower the potential of the solution if the measurement voltage is higher than the reference voltage.

8. A 3-electrode type measurement apparatus comprising:
a working electrode configured to cause electrode reactions of an object to be analyzed in a solution;
a counter electrode disposed to face the working electrode;
a reference potential measuring unit configured to measure a potential of the solution; and
a comparator configured to compare a measurement voltage provided by the reference potential measuring unit to a reference voltage provided by a reference voltage supply unit, and to adjust reactions of the counter electrode with the solution according to the result of the comparison,
wherein the reference potential measuring unit includes a field effect device configured to change conductivity of charges flowing through the reference potential measuring unit according to the potential of the solution.

9. The 3-electrode type measurement apparatus of claim 8, wherein the field effect device includes carbon nanotubes (CNTs) or graphene whose electrical conductivity changes according to the potential of the solution.

10. The 3-electrode type measurement apparatus of claim 9, wherein the field effect device includes a channel layer comprising the CNTs or the graphene contacting the solution, and both ends of the channel layer are connected to electrode layers.

11. The 3-electrode type measurement apparatus of claim 8, further comprising a voltage converter connected to an input terminal of the comparator, and configured to provide the measurement voltage that is calculated in correspondence to an amount of charges flowing through the field effect device of the reference potential measuring unit.

12. The 3-electrode type measurement apparatus of claim 11, wherein the voltage converter includes a voltage converter resistor, and creates the measurement voltage from the amount of charges, based on a resistance value of the voltage converter resistor and a resistance value of a channel layer of the field effect device.

13. The 3-electrode type measurement apparatus of claim 8, wherein the comparator compares the measurement voltage to the reference voltage,
adjusts reactions of the counter electrode with the solution to raise the potential of the solution if the measurement voltage is lower than the reference voltage, and
adjusts reactions of the counter electrode with the solution to lower the potential of the solution if the measurement voltage is higher than the reference voltage.

14. The 3-electrode type measurement apparatus of claim 8, further comprising a driving voltage supply unit configured to apply a driving voltage for causing electrode reactions of an object to be analyzed between the working electrode and the counter electrode.

15. A sensor comprising:
a sensing apparatus and a reference potential adjusting apparatus,
wherein the sensing apparatus comprises:
a first electrode disposed on a substrate;
a second electrode spaced apart from the first electrode; and
at least one nano structure contacting the first electrode and the second electrode, and having electrical characteristics changing according to an object to be sensed in a solution, and
the reference potential adjusting apparatus comprises:
a counter electrode disposed in the solution, and configured to change a potential of the solution through oxidation-reduction reactions with the solution;
a reference potential measuring unit configured to measure the potential of the solution; and
a comparator configured to compare a measurement voltage provided by the reference potential measuring unit to a reference voltage provided by a reference voltage supply unit, and to generate a control signal for adjusting reactions of the counter electrode with the solution according to the result of the comparison, the reference potential measuring unit including a field effect device configured to change conductivity of charges flowing through the reference potential measuring unit according to the potential of the solution.

16. The sensor of claim 15, wherein the field effect device comprises:
a reference electrode;
a common electrode disposed to be spaced apart from the reference electrode; and
a channel layer contacting the reference electrode and the common electrode, and having electrical conductivity changing according to the potential of the solution.

17. The sensor of claim 15, wherein the reference electrode is one of the first electrode and the second electrode, and the common electrode is the other of the first electrode and the second electrode.

18. The sensor of claim 16, wherein the channel layer includes substantially the same material as the at least one nano structure.

19. The sensor of claim 15, wherein the nano structure includes at least one selected from the group consisting of a metal, a metal oxide, a semiconductor, and a conductive polymer.

20. The sensor of claim 19, wherein the nano structure includes a carbon nanotube (CNT) or graphene.

21. The sensor of claim 15, wherein the nano structure has a shape selected from the group consisting of a nanotube, a nanowire, a nanorod, a nanoribbon, a nanofilm, and a nanoball.

22. The sensor of claim 16, further comprising a voltage converter connected to an input terminal of the comparator, and configured to provide the measurement voltage that is calculated in correspondence to an amount of charges flowing through the at least one nano structure of the reference electrode.

23. The sensor of claim 15, wherein the sensing apparatus has an array structure including a first electrode and a second electrode spaced apart from the first electrode.

* * * * *